(12) United States Patent
Billington et al.

(10) Patent No.: US 8,557,866 B2
(45) Date of Patent: Oct. 15, 2013

(54) ISOMERIC MIXTURES OF DINITRO-OCTYLPHENYL ESTERS AND SYNERGISTIC FUNGICIDAL MIXTURES THEREFROM

(75) Inventors: Richard Billington, Wantagae (GB); John Davies, Midland, MI (US); Bernhard Distler, Bad Ailbling (DE); Robert J. Ehr, Indianapolis, IN (US); Franco Sivieri, Treviglio (IT); Elizabeth Green, East Hagbourne (GB); John T. Mathieson, Brownsburg, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 753 days.

(21) Appl. No.: 11/786,899

(22) Filed: Apr. 13, 2007

(65) Prior Publication Data

US 2008/0255233 A1    Oct. 16, 2008

(51) Int. Cl.
*A01N 37/06*    (2006.01)
*A61K 31/22*    (2006.01)

(52) U.S. Cl.
USPC .................. 514/549; 514/260.1; 504/118

(58) Field of Classification Search
USPC .................. 514/549, 260.1; 504/118
See application file for complete search history.

(56) References Cited

U.S. PATENT DOCUMENTS

| | | | | |
|---|---|---|---|---|
| 3,284,293 | A | * | 11/1966 | Mohr et al. .................. 514/344 |
| 3,715,384 | A | | 2/1973 | Pianka et al. |
| 3,822,357 | A | * | 7/1974 | Von Meyer .................... 14/728 |
| 5,536,734 | A | * | 7/1996 | Mueller et al. ................ 514/336 |
| 2005/0227956 | A1 | * | 10/2005 | Wang et al. .................... 514/184 |
| 2005/0239805 | A1 | * | 10/2005 | Geddens et al. ........... 514/260.1 |

FOREIGN PATENT DOCUMENTS

| | | | |
|---|---|---|---|
| GB | 1113783 | * | 8/1965 |
| WO | WO-03/103393 | * | 12/2003 |
| WO | WO 03/103393 A1 | | 12/2003 |
| WO | PCT/US2005/036679 | | 2/2006 |

OTHER PUBLICATIONS

Kartal, S.N., Preliminary evaluation of fungicidal and termiticidal activities of filtrates from biomass slurry fuel production, Elsevier, Bioresource Technology 95, 2004, p. 41-47.*
Kartal, S.N. et al., Preliminary evaluation of fungicidal and termicidal activities of filtrates from biomass slurry fuel production, Bioresource Technology, vol. 95, Issue 1, Oct. 2004, pp. 21-27.
Rogers, John M. et al., Developmental Toxicity of Dinocap in the Mouse is not Due to Two Isomers of the Major Active Ingredients, Teratogenesis, Carcinogenesis, and Mutagenesis 7:341-346 (1987).
PPR Panel Opinion; Question No. EFSA-Q-2004-26; The EFSA Journal (2004) 74, 1-23.
Gray, Jr. Earl et al., Prenatal Dinocap exposure alters Swimming Behavior in Mice Due to Complete Otolith Agenesis in the Inner Ear, Toxicology and Applied Pharmacology 92, 255-273 (1988).

* cited by examiner

*Primary Examiner* — Fereydoun G Sajjadi
*Assistant Examiner* — Danielle Sullivan
(74) *Attorney, Agent, or Firm* — C. W. Arnett

(57) ABSTRACT

The present invention relates to an isomeric composition comprising isomers of dinitro-octylphenyl esters, wherein the 2,6-dinitro-4-(1-propylpentyl)phenyl ester isomer is present in an amount of less than 0.1 weight percent, based on the total weight of the isomeric composition and to synergistic fungicidal mixtures therefrom.

12 Claims, No Drawings

ISOMERIC MIXTURES OF DINITRO-OCTYLPHENYL ESTERS AND SYNERGISTIC FUNGICIDAL MIXTURES THEREFROM

CROSS-REFERENCE TO RELATED APPLICATIONS

This application claims the benefit of International Patent application No. PCT/US2005/036679, filed Oct. 14, 2005, which claims the benefit of U.S. Provisional Patent Application Ser. No. 60/618,919, filed Oct. 14, 2004, U.S. Provisional Patent Application Ser. No. 60/624,704, filed Nov. 3, 2004, and U.S. Provisional Patent Application Ser. No. 60/695,232, filed Jun. 29, 2005, all of which are expressly incorporated by reference herein.

The present invention relates to isomeric compositions of dinitro-octylphenyl esters and synergistic fungicidal compositions.

Compositions comprising 2,4-dinitro-6-octylphenyl crotonates and 2,6-dinitro-4-octylphenyl crotonates have been used as fungicides for control of powdery mildew, or certain species of plant parasitic mites. Such compositions, also known as dinocap, are the active ingredients used in Karathane™ Fungicide/Miticide. Dinocap is a mixture of six isomers, each having a cis and trans component, and contains as its active ingredients a mixture of 2,4- and 2,6-dinitro-octylphenyl crotonates in an approximate 2:1 ratio, wherein 'octyl' refers to a mixture of 1-methylheptyl, 1-ethylhexyl, and 1-propylpentyl isomers. Various studies have been published relating to 2,4-dinitro-6-(1-methylheptyl)phenyl crotonate, including a report on the dermal absorption and mammalian developmental effects of dinocap. "Dinocap Dermal Absorption in Female Rabbits and Rhesus Monkeys", *Biological Monitoring for Pesticide Exposure*, Chapter 11, pages 137-151, Dec. 4, 1987, discloses a study related to absorption data for 2,4-dinitro-6-(1-methylheptyl)phenyl crotonate isomer at 97 percent purity. Another study, "Developmental Toxicity of Dinocap in the Mouse is Not Due to Two Isomers of the Major Active Ingredients", *Teratogenesis, Carcinogenesis, and Mutagenesis* 7:341-346 (1987) reports the use of Dinocap as a fungicide and reports toxicity data for 2,4-dinitro-6-(1-methylheptyl)phenyl crotonate isomer at 95 percent purity.

Dinocap is known to form synergistic mixtures with other fungicides, including mixtures with benzophenones as taught in WO 02/067679 and U.S. Pat. No. 6,346,535; with phenylbenzylethers and/or carbamates as taught in U.S. Pat. No. 6,528,536; with amides as taught in U.S. Pat. No. 6,515,000; with benzamidoximes as taught in WO 2004091298; with 1-((N-(2,3-dichloro-4-hydroxyphenyl)amino)-carbonyl)-1-methyl cyclohexanes as taught in U.S. Pat. No. 6,207,691; with chlorothalonil and ditalimfos as taught in FR 2445696; with N-(p-fluorophenyl)-2,3-dichloromaleimide as taught in GB 2003032; with tetrachloroisophthalonitrile as taught in U.S. Pat. No. 3,456,055; with phenylbenzylethers or carbamates as taught in U.S. Pat. No. 6,489,360; with aminomethyl heterocycles as taught in U.S. Pat. No. 5,569,656; with fused pyrimidinones as taught in WO2003103393; and the like, wherein all of the U.S. patents recited above are incorporated herein by reference.

Dinocap is a mixture of isomers with varying levels of toxicological effects, e.g. teratogenicity in mice and retinopathy in dogs. Thus, there continues to be a need to produce similar fungicides having more favorable toxicological properties, while maintaining or increasing fungicidal efficacy and in developing synergistic fungicidal mixtures therefrom.

The present invention relates to an isomeric composition comprising isomers of dinitro-octylphenyl esters, wherein the 2,6-dinitro-4-(1-propylpentyl)phenyl ester isomer is present in an amount of less than 0.1 weight percent, based on the total weight of the isomeric composition; and to synergistic fungicidal mixtures therefrom.

It has been surprisingly discovered that the isomeric composition of the present invention containing less than 0.1 weight percent 2,6-dinitro-4-(1-propylpentyl)phenyl ester isomer has very favorable toxicological properties while maintaining fungicidal efficacy.

Typically, a dinitro-octylphenyl ester exists as a mixture of isomers which include forms of the following isomers:
2,4-dinitro-6-(1-methylheptyl)phenyl ester,
2,4-dinitro-6-(1-ethylhexyl)phenyl ester,
2,4-dinitro-6-(1-propylpentyl)phenyl ester,
2,6-dinitro-4-(1-methylheptyl)phenyl ester,
2,6-dinitro-4-(1-ethylhexyl)phenyl ester, and
2,6-dinitro-4-(1-propylpentyl)phenyl ester;
wherein the ester is defined as any ester functional group which is capable of hydrolyzing under environmental conditions to form the corresponding phenol. Environmental conditions include those conditions which occur naturally in the environment of agricultural crops or within the crops themselves, including the presence of moisture.

It has been surprisingly discovered that an isomeric composition comprising less than 0.1 weight percent of 2,6-dinitro-4-(1-propylpentyl)phenyl ester, based on the total weight of the isomeric composition, has no teratogenic or retinopathic effects, while maintaining fungicidal efficacy.

For example, dinocap is an isomeric composition which refers to a mixture of isomers of dinitro-octylphenyl crotonates which include both cis and trans forms of the following isomers:
2,4-dinitro-6-(1-methylheptyl)phenyl crotonate,
2,4-dinitro-6-(1-ethylhexyl)phenyl crotonate,
2,4-dinitro-6-(1-propylpentyl)phenyl crotonate,
2,6-dinitro-4-(1-methylheptyl)phenyl crotonate,
2,6-dinitro-4-(1-ethylhexyl)phenyl crotonate, and
2,6-dinitro-4-(1-propylpentyl)phenyl crotonate.

It is well known in the art that the crotonate ester, as in dinocap, hydrolyzes with exposure to the plant or environment to the corresponding dinitro-octylphenol and that the phenol is the active ingredient having fungicidal effects. Therefore, any ester or analog of these compounds in which the ester is derivatized to form a related substituent that can be transformed within plants or the environment to the phenol, possess essentially the same fungicidal effect and are within the scope of the present invention. Preferably, the isomeric composition of the present invention is a mixture of dinitro-octylphenyl crotonates.

In general, the isomeric composition of the present invention can comprise a dinitro-octylphenyl ester in any combination and amounts of isomers, as long as the amount of 2,6-dinitro-4-(1-propylpentyl)phenyl ester is below 0.1 weight percent based on the total weight of the isomeric composition and as long as the improved toxicology and fungicidal efficacy is maintained. In other words, the isomeric composition can comprise any number of dinitro-octylphenyl ester isomers, each isomer in any amount, so long as the amount of 2,6-dinitro-4-(1-propylpentyl)phenyl ester is below 0.1 weight percent based on the total weight of the isomeric composition. Generally, the isomeric composition will comprise:
from 0.1 to 99.9 weight percent 2,4-dinitro-6-(1-methylheptyl)phenyl ester, from 0.1 to 99.9 weight percent 2,4-dinitro-6-(1-ethylhexyl) phenyl ester, from 0.1 to 99.9 weight percent 2,4-dinitro-6-(1-propylpentyl)phenyl ester, from 0.1 to 99.9 weight percent 2,6-dinitro-4-(1-methylheptyl)phenyl ester, from 0.1 to 99.9 weight percent 2,6-dinitro-4-(1-ethylhexyl) phenyl ester, and less than 0.1 weight percent 2,6-dinitro-4-(1-propylpentyl) phenyl ester.

In one embodiment, the isomeric composition of the present invention comprises at least 20, generally at least 30, more generally at least 40, typically at least 50, more typically at least 60, preferably at least 70, more preferably at least 80, even more preferably at least 90 and most preferably at least 95 weight percent 2,4-dinitro-6-(1-methylheptyl)phenyl ester, based on the total weight of all of the isomers which are present in the composition.

In another embodiment, the isomeric composition of the present invention comprises from 1, generally from 1.5, typically from 2, preferably from 2.5, more preferably from 3 and most preferably from 5 to 45, generally to 40, typically to 35, preferably to 30, more preferably to 27 and most preferably to 25 weight percent 2,4-dinitro-6-(1-ethylhexyl)phenyl ester, based on the total weight of all of the isomers which are present in the composition.

In another embodiment, the isomeric composition of the present invention comprises from 0.1, generally from 0.5, typically from 1, preferably from 1.5, more preferably from 2.0 and most preferably from 2.5 to 45, generally to 40, typically to 35, preferably to 30, more preferably to 27 and most preferably to 25 weight percent 2,4-dinitro-6-(1-propylpentyl)phenyl ester, based on the total weight of all of the isomers which are present in the composition.

In yet another embodiment, the isomeric composition of the present invention comprises from 0.1, generally from 0.5, typically from 0.7, preferably from 1.0, more preferably from 1.5 and most preferably from 2.0 to 45, generally to 40, typically to 35, preferably to 30, more preferably to 27 and most preferably to 25 weight percent 2,6-dinitro-4-(1-methylheptyl)phenyl ester, based on the total weight of all of the isomers which are present in the composition.

In another embodiment, the isomeric composition of the present invention comprises 0.1, generally from 0.5, typically from 1.0, preferably from 1.5, more preferably from 2.0 and most preferably from 2.5 to 45, generally to 40, typically to 35, preferably to 30, more preferably to 27 and most preferably to 25 weight percent or less 2,4-dinitro-6-(1-ethylhexyl) phenyl ester.

The isomeric composition of the present invention comprises less than 0.1, generally, less than 0.08, more generally, less than 0.06, preferably less than 0.04, more preferably less than 0.02 and most preferably less than 0.001 weight percent of 2,6-dinitro-4-(1-propylpentyl)phenyl ester. In a most preferred embodiment, the isomeric composition of the present invention is a mixture of isomers in the absence of 2,6-dinitro-4-(1-propylpentyl)phenyl ester. 'The absence of' refers to an undetectable amount as measured using High Pressure Liquid Chromatography.

In another embodiment of the present invention, the isomeric compositions comprise:

from 80 to 98 weight percent 2,4-dinitro-6-(1-methylheptyl) phenyl ester, less than 1.5 weight percent 2,4-dinitro-6-(1-ethylhexyl)phenyl ester, less than 0.1 weight percent 2,4-dinitro-6-(1-propylpentyl) phenyl ester, less than 0.1 weight percent 2,6-dinitro-4-(1-methylheptyl) phenyl ester, less than 0.1 weight percent 2,6-dinitro-4-(1-ethylhexyl)phenyl ester, and less than 0.1 weight percent 2,6-dinitro-4-(1-propylpentyl) phenyl ester.

The isomeric composition of the present invention can be made by a variety of methods as long as the final isomeric composition contains less then 0.1 wt. percent of 2,6-dinitro-4-(1-propylpentyl)phenyl ester. Dinocap is typically obtained by conversion of a mixture of dinitro-octylphenols to dinitro-octylphenyl crotonates by reaction with crotonyl chloride, as is well known in the art and described in "E.Y. Guide to the Chemicals Used in Crop Protection." 7th ed. Publication 1093, Research Institute, Agriculture Canada, Ottawa, Canada: Information Canada, 1982. 229. Other esters can also be made by substituting the appropriate material for the crotonyl chloride in order to place a different ester on the phenyl ring. The isomeric composition can be obtained using the above process by utilizing a mixture of dinitro-octylphenols, containing less than 0.1 weight percent 2,6-dinitro-4-(1-propylpentyl)phenol in the reaction, which can in turn be produced by the dinitration of octylphenols containing less than 0.1 weight percent 4-(1-propylpentyl)phenol. Highly pure starting materials can be obtained by any known process including purification and separation processes necessary to achieve the desired purity. For example, methods contemplated include any known method for producing 2,4-dinitro-6-(1-methylheptyl)phenol or any isomer of 2,4-dinitro-6-octylphenol, 2,6-dinitro-4-octylphenol, or mixture thereof, followed by appropriate purification and/or separation methods in order to obtain the desired highly pure starting material having less than 0.1 weight percent 2,6-dinitro-4-(1-propylpentyl)phenol. Alternatively, highly pure methylheptyl phenol can be nitrated to produce a highly pure dinitro-octylphenol. Highly pure methylheptyl phenol can be obtained by any known process for alkylating phenol, followed by purification such as distillation, chromatography and the like.

Still other methods contemplated herein include any known method for producing isomeric mixtures of 2,4-dinitro-6-octylphenyl esters and 2,6-dinitro-4-octylphenyl esters, followed by appropriate purification and/or separation methods in order to obtain the isomeric composition of the present invention. Purification and separation techniques can be any known technique to one skilled in the art, including distillation, chromatography, and the like. Other related methods of producing such isomeric mixtures also include those disclosed in U.S. Pat. No. 2,810,767 and U.S. Pat. No. 2,526,660, which are both incorporated herein by reference.

In one embodiment, 2,4-dinitro-6-(1-methylheptyl)phenol having a purity of at least 98.5 percent and having less than 0.1 weight percent 2,6-dinitro-4-(1-propylpentyl)phenol is utilized in preparing the isomeric composition of the present invention.

Additionally, another embodiment of the present invention is a fungicidal composition, useful for protecting a plant against attack by a phytopathogenic organism and/or treatment of a plant infested by a phytopathogenic organism, comprising I) an isomeric composition of dinitro-octylphenyl esters containing less than 0.1 weight percent of 2,6-dinitro-4-(1-propylpentyl)phenyl esters, based on the total weight of the isomeric composition, and II) a phytologically acceptable carrier material.

The isomeric composition of the present invention contemplates all vehicles by which the isomeric composition can be formulated for delivery and used as a fungicide. Typically, formulations are applied as aqueous suspensions or emulsions. Such suspensions or emulsions are produced from water-soluble, water suspendable, or emulsifiable formulations which are (1) solids, usually known as wettable powders or water dispersible granules or (2) liquids, usually known as emulsifiable concentrates, aqueous emulsions, suspension concentrates and water suspended capsules containing the isomeric composition. As will be readily appreciated, any material to which the isomeric composition can be added may be used, provided they yield the desired utility without significant interference with the activity of the isomeric composition as antifungal agents.

Wettable powders, which may be compacted, extruded or processed through a dispersion in water followed by spray drying or fluid bed agglomeration to form water dispersible granules, comprise an intimate mixture of the isomeric composition, an inert carrier and surfactants. The concentration of the isomeric composition in the wettable powder is usually from 10 percent to 90 percent by weight based on the total weight of the wettable powder, more preferably 25 wt. percent to 75 wt. percent. In the preparation of wettable powder formulations, the isomeric composition can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the isomeric composition and milled.

Emulsifiable concentrates of the isomeric composition comprise a convenient concentration, such as from 5 wt. percent to 75 wt. percent of the isomeric composition, in a suitable liquid, based on the total weight of the concentrate. The isomeric composition is dissolved in an inert carrier, which is either water, a water miscible solvent, a water immiscible solvent, or a mixture thereof and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyokyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulfated polyglycol ethers and appropriate salts of phosphated polyglycol ether.

Representative organic liquids which can be employed in preparing the emulsifiable concentrates of the isomeric composition are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Preferred organic liquids include xylene, and propyl benzene fractions, with propylbenzene fractions being most preferred. Surface-active emulsifying agents are typically employed in liquid formulations and in an amount of from 0.1 to 20 percent by weight based on the combined weight of the emulsifying agent with the isomeric composition. The formulations comprising the isomeric composition of the present invention can also contain other compatible additives, for example, miticides, insecticides, plant growth regulators, other fungicides, and other biologically active compounds used in agriculture.

Aqueous suspensions comprise suspensions of the isomeric composition, dispersed in an aqueous vehicle at a concentration in the range from 5 to 50 weight percent, based on the total weight of the aqueous suspension. Aqueous suspensions are prepared by vigorously mixing the isomeric composition of the present invention, or its solution, into a vehicle comprised of water and surfactants chosen from the same types discussed above. Other components, such as inorganic salts and synthetic or natural gums, may also be added to increase the density and viscosity of the aqueous vehicle. Examples of aqueous suspensions include suspensions of oil droplets (EW's), solids (SC's), and capsules (CS's).

The isomeric composition can also be applied as granular formulations, which are particularly useful for applications to the soil. Granular formulations usually contain from 0.5 to 10 wt. percent, based on the total weight of the granular formulation of the isomeric composition, dispersed in an inert carrier which consists entirely or in large part of coarsely divided inert material such as attapulgite, bentonite, diatomite, clay or a similar inexpensive substance. Such formulations are usually prepared by diluting the isomeric composition in a suitable solvent and applying it to a granular carrier which has been preformed to the appropriate particle size, in the range of from 0.5 to 3 mm. A suitable solvent is a solvent in which the compound is substantially or completely soluble. Such formulations may also be prepared by making a dough or paste of the carrier and the isomeric composition and solvent, and crushing and drying to obtain the desired granular particle.

The isomeric composition of the present invention can also be applied as a water dispersible granule, or dry flowable formulation. Water dispersible granules typically contain from 10 to 70 percent of the isomeric composition, based on the total weight of the formulation. Such formulations are typically obtained through mixing and/or spraying the isomeric mixture onto a carrier with the addition of a dispersing and/or wetting agent, and combining with water to form a mixture suitable for further processing using well known granulation technologies, such as pan granulation, extrusion, spray-drying, fluid bed agglomeration, and the like.

Dusts containing the isomeric composition can be prepared by intimately mixing the isomeric composition with a suitable dusty agricultural carrier, such as, for example, kaolin clay, ground volcanic rock, and the like. Dusts can suitably contain from 1 to 10 wt. percent of the isomeric composition or other fungicide, based on the total weight of the dust. Dusts may also be prepared by impregnating the isomeric composition onto a carrier in a similar manner to that described for granules above.

The formulations of the present invention may additionally contain adjuvant surfactants to enhance deposition, wetting and penetration of the isomeric composition onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

One embodiment of the present invention relates to a synergistic mixture of fungicides comprising the isomeric composition of the present invention and at least one other fungicide, and its' use for protection of a plant against attack by a phytopathogenic organism or the treatment of a plant already infested by a phytopathogenic organism, comprising applying the synergistic mixture, to soil, a plant, a part of a plant, foliage, flowers, and/or fruit.

Fungicidal compounds are often applied in conjunction with one or more other fungicides to control a wider variety of undesirable diseases. When used in conjunction with other fungicide(s), the presently claimed isomeric composition can be formulated with the other fungicide(s), tank mixed with the other fungicide(s) or applied sequentially with the other fungicide(s). Such other fungicides include amisulbrom 2-(thiocyanatomethylthio)-benzothiazole, 2-phenylphenol, 8-hydroxyquinoline sulfate, antimycin, Ampelomyces quisqualis, azaconazole, azoxystrobin, Bacillus subtilis, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), coumarins, cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, SYP-048, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazolopyrimidine, triazoxide, tricyclazole, tridemorph, trifloxystrobin, triflumizole, triforine, triticonazole, validamycin, vinclozolin, zineb, ziram, zoxamide, Candida oleophila, Fusarium oxysporum, Gliocladium spp., Phlebiopsis gigantean, Streptomyces griseoviridis, Trichoderma spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, IK-1140, NC-224, and any combinations thereof.

Synergy has been found previously with dinocap as disclosed in references such as, but not limited to WO 02/067679; WO2003103393; WO 2004091298; FR 2445696; GB 2003032; U.S. Pat. No. 6,346,535; U.S. Pat. No. 6,528,536; U.S. Pat. No. 6,515,000; U.S. Pat. No. 6,207,691; U.S. Pat. No. 3,456,055; and U.S. Pat. No. 6,489,360. However, synergies with the composition of the present invention have not been previous reported.

Another aspect of the present invention is related to synergistic mixtures of the isomeric composition described herein with at least one other fungicide, which surprisingly have improved toxicity properties. The synergistic composition of the present invention can comprise 1) any fungicide which is synergistic with dinocap and 2) the isomeric composition as detailed herein. Exemplary fungicides known to show synergistic effects include, but are not limited to, QoI fungicides such as, methoxyacrylates including azoxystrobin, and oximino acetates including kresoxim methyl; SBI fungicides: class I such as triazoles including myclobutanil; class II such as spiroketal-amines including spiroxamine; and class III such as hydroxyanilides including fenhexamid; benzophenones such as metrafenone; quinolines such as quinoxyfen; dithiocarbamates and derivatives such as mancozeb; chloronitriles such as chlorothalonil; respiration inhibition at complex II succinate dehydrogenase carboxamides including boscalid, and the like.

In one specific embodiment, the present invention is a synergistic mixture comprising:

i) an isomeric composition comprising isomers of dinitro-(octyl)phenyl esters, wherein the 2,6-dinitro-4-(1-propylpentyl)phenyl ester isomer is present in an amount of less than 0.1 weight percent, based on the total weight of the isomeric composition, and ii) QoI fungicide (commonly referred to as strobilurins and related chemistry).

QoI fungicides include compounds such as azoxystrobin, dimoxystrobin, fluoxastrobin, orysastrobin, picoxystrobin, pyraclostrobin, trifloxystrobin, kresoxim-methyl, famoxadone, fenamidone and the like.

In another embodiment, the present invention is a synergistic mixture comprising:

i) an isomeric composition comprising isomers of dinitro-(octyl)phenyl esters, wherein the 2,6-dinitro-4-(1-propylpentyl)phenyl ester isomer is present in an amount of less than 0.1 weight percent, based on the total weight of the isomeric composition, and ii) a quinoline or cinnoline.

Quinolines and cinnolines, such as Quinoxyfen are reported in U.S. Pat. No. 5,145,843, which is incorporated herein by reference.

In another embodiment, the present invention is a synergistic mixture comprising:

i) an isomeric composition comprising isomers of dinitro-(octyl)phenyl esters, wherein the 2,6-dinitro-4-(1-propylpentyl)phenyl ester isomer is present in an amount of less than 0.1 weight percent, based on the total weight of the isomeric composition, and ii) a dithiocarbamate.

Dithiocarbamates include compounds such as mancozeb (a coordination product of zinc and manganese ethylene bis-dithiocarbamate), maneb (manganese ethylenebisdithio-carbamate) and zineb (zinc ethylenebisdithiocarbamate), ziram (zinc dimethyldithio-carbamate), propineb ([[1-methyl-1,2-ethanediyl)bis[carbamatothioato]](2-)]zinc homopolymer), metiram)(tris[amine-[ethylene bis(dithiocarbamate)]-zinc (II)-[tetrahydro-1,2,4,7-dithiadia-zocine-3,8-dithione]polymer), ferbam (ferric dimethyldithiocarbamate), metham (sodium N-methyldithiocarbamate), and thiram (bis(dimethylthiocarbamoyl) disulfide) and the like.

In another embodiment, the present invention is a synergistic mixture comprising:

i) an isomeric composition comprising isomers of dinitro-(octyl)phenyl esters, wherein the 2,6-dinitro-4-(1-propylpentyl)phenyl ester isomer is present in an amount of less than 0.1 weight percent, based on the total weight of the isomeric composition, and ii) a triazole.

Triazoles include compounds such as azaconazole, bitertanol, bromuconazole, chlorfenazole, climbazole, cypendazole, cyproconazole, diclobutrazol, difenoconazole, diniconazole, diniconazole-M, epoxiconazole, etaconazole, etridiazole, fenbuconazole, fluotrimazole, fluquinconazole, flusilazole, flutriafol, fuberidazole, furconazole, and furconazole-cis. hexaconazole, imazalil, imibenconazole, ipconazole, metconazole, myclobutanil, pefurazoate, penconazole, probenazole, prochloraz, propiconazole, prothioconazole, quinconazole, rabenzazole, simeconazole, tebuconazole, tetraconazole, triadimefon, triadimenol, tricyclazole, triflumazole, triticonazole and the like.

In another embodiment, the present invention is a synergistic mixture comprising:

i) an isomeric composition comprising isomers of dinitro-(octyl)phenyl esters, wherein the 2,6-dinitro-4-(1-propylpentyl)phenyl ester isomer is present in an amount of less than 0.1 weight percent, based on the total weight of the isomeric composition, and ii) spiroxamine.

The amount of the isomeric mixture and other fungicide within the synergistic mixture can vary depending on the application desired and diseases for desired control. Generally, the isomeric composition is present in amounts of from 0.1, more generally from 1, even more generally from 5, most generally from 10, typically from 15, more typically from 20, even more typically from 30, most typically from 40, and routinely from 45 weight percent to generally 99.9, more generally to 99, even more generally to 95, most generally to 90, typically to 85, more typically to 80, even more typically to 70, most typically to 60, and routinely to 55 weight percent based on the total weight of the isomeric composition and other fungicide(s).

Generally, the at least one other fungicide is present in amounts of from 99.9, more generally 99, even more generally 95, most generally 90, typically 85, more typically 80, even more typically 70, most typically 60, and routinely 55 to 0.1, more generally 1, even more generally 5, most generally 10, typically 15, more typically 20, even more typically 30, most typically 40, and routinely 45 weight percent based on the total weight of the isomeric composition and other fungicide(s).

Additionally, the isomeric compositions and synergistic mixtures can be combined with other pesticides including insecticides, nematocides, miticides, arthropodicides, bactericides or combinations thereof that are compatible with the isomeric composition in the medium selected for application, and not antagonistic to the activity of the isomeric composition. Accordingly, in such embodiments, the other pesticidal compound is employed as a supplemental toxicant for a different pesticidal use. When used in conjunction with other pesticides, the isomeric composition or synergistic mixture can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen, spirodiclofen and spirotetramet; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridine, pyridaben, pyridalyl, rafoxanide, triarathene and triazamate, and any combinations thereof.

The amount of the isomeric composition or synergistic mixture thereof, and other pesticide within a pesticidal mixture can vary depending on the application desired and diseases for desired control. Generally, the isomeric composition or synergistic mixture of the present invention is present in amounts of from 0.1, more generally from 1, even more generally from 5, most generally from 10, typically from 15, more typically from 20, even more typically from 30, most typically from 40, and routinely from 45 weight percent to generally 99.9, more generally to 99, even more generally to 95, most generally to 90, typically to 85, more typically to 80, even more typically to 70, most typically to 60, and routinely to 55 weight percent, based on the total weight of the isomeric composition or synergistic mixture and other pesticide(s).

Generally, when employed, the other pesticide is present in amounts of from 99.9, more generally 99, even more generally 95, most generally 90, typically 85, more typically 80, even more typically 70, most typically 60, and routinely 55 to 0.1, more generally 1, even more generally 5, most generally 10, typically 15, more typically 20, even more typically 30, most typically 40, and routinely 45 weight percent, based on the total weight of the isomeric composition or synergistic mixture and other fungicide(s).

Another embodiment of the present invention is a method for the control or prevention of fungal attack. This method comprises applying to the plant, foliage, locus of the fungus, or to a locus in which the infestation is to be prevented (for example applying to cereal or grape plants), a fungicidal effective amount of the isomeric composition or synergistic mixture therefrom. The isomeric composition or synergistic mixture of the present invention is suitable for treatment of various plants at fungicidal levels, while exhibiting no teratogenicity or retinopathy. The isomeric composition or synergistic mixture is useful both in a protectant, curative and/or an eradicant fashion.

The isomeric composition and synergistic mixture therefrom have been found to have significant fungicidal effect particularly for agricultural use and is particularly effective for use with agricultural crops and horticultural plants. In particular, the isomeric composition and synergistic mixture therefrom effectively controls a variety of undesirable fungi that infect useful plant crops, such as powdery mildews in pome fruit, stone fruit, citrus fruit, soft fruit, vines, cucurbits, ornamentals, tobacco, hops, and some vegetables, and American gooseberry mildew in gooseberries and currants.

The exact amount of isomeric composition or synergistic mixture therefrom to be applied is dependent on the particular action desired, the fungal species to be controlled, the stage of growth thereof, as well as the part of the plant or other product to be contacted with the isomeric composition.

The isomeric composition and synergistic mixture therefrom are effective in use with plants in a disease-inhibiting and phytologically acceptable amount. The term "disease inhibiting and phytologically acceptable amount" refers to an amount of an active compound that kills or inhibits the plant disease for which control is desired, but is not significantly toxic to the plant. This amount will generally be from 1 to 1000 ppm (parts per million), with 10 to 500 ppm being preferred. The exact concentration of isomeric composition or synergistic mixture required varies with the fungal disease to be controlled, the type of formulations employed, the method of application, the particular plant species, climate conditions, and the like. A suitable application rate is typically in the range from 0.10 to 4 pounds/acre (0.01 to 0.45 grams per square meter $g/m^2$).

It has also been surprisingly discovered that the isomeric composition and synergistic mixtures therefrom of the present invention can have a decreased acaracidal effect, which is advantageous in maintaining beneficial mites.

EXAMPLES

These examples are provided to further illustrate the invention and are not meant to be construed as limiting. As disclosed herein, all temperatures are given in degrees Celsius and all percentages are weight percentages, except for percent yields which are mole percentages, unless otherwise stated.

Preparation of 2,4-Dinitro-6-(1-methylheptyl)phenol 2-(1-methylheptyl)phenol (206.3 gm, 98.5 percent assay) is stirred and heated to 60° C. Concentrated sulfuric acid (315.2 gm) is added dropwise over 1 hour, maintaining the temperature in the range 65-72° C.

In a separate vessel, a 35 percent aqueous solution of sodium nitrate (553.2 gm) is stirred and heated to 70° C. The sulfonated phenol reaction mixture is then added dropwise, over 3 hours to the sodium nitrate solution, maintaining the temperature at 78° C. The mixture is stirred at 78° C. for one hour, and then cooled to 35° C. The mixture is allowed to settle, and the aqueous layer separated. The organic layer is washed twice with water containing a little methanol, and then dried under vacuum at 75° C. to leave 252 gm of 2,4-dinitro-6-(1-methylheptyl)phenol product as an orange oil.

Example 1

Preparation of 2,4-dinitro-6-(1-methylheptyl)phenyl crotonate 2,4-Dinitro-6-(1-methylheptyl)phenol (98.5 percent pure) (252 gm) is dissolved in heptane (225 gm). Benzyldimethylamine (140.8 gm) is added dropwise over 40 minutes, keeping the temperature of the mixture below 40° C., and the mixture is stirred for 15 minutes. Crotonyl chloride (139 gm) is then added dropwise over 30 minutes, keeping the temperature below 60° C., and the mixture is stirred at 60° C. for 30 minutes and cooled to less than 50° C. The mixture is washed twice with water and then cooled to 20° C. The mixture is washed with a mixture of methanol and aqueous sodium hydroxide, with water and methanol, and finally with dilute hydrochloric acid. The organic layer is stripped at 70° C. under vacuum to remove heptane and leave 2,4-dinitro-6-(1-methylheptyl)phenyl crotonate (282.6 gm) as an orange/brown oil.

For analysis, normal phase liquid chromatography is utilized using the following method:
HPLC Conditions
Column temp 40° C.
Flow volume 1 ml/min
Wavelength 235 nm
Injection volume 10 microliters
HPLC Milton Roy Column 250×4.6 mm, packed with 7μ LICHROSORB S160 (Merck)
Detection: Detector Milton Roy SM 4000
Integration system Shimadzu Mega2.
Sample Solution:
A 0.45-0.50 g sample of 2,4-dinitro-6-(1-methylheptyl)phenyl crotonate and 0.09-0.11 g of acetophenone is placed in a vial. Hexane (20 ml), is added, the vial is capped and sonicated for 2 minutes. The solution (1 ml) is transferred into a vial and 20 ml of hexane is added, the vial capped and shaken to produce a sample solution.
Standard Solution:
0.48-0.52 g of Karathane™ Working Standard and 0.09-0.11 g of acetophenone (I.S.) are placed into a vial. Hexane (20 ml), is added, the vial is capped and sonicated for 2 minutes. The solution (1 ml) is transferred into a vial and 20 ml of hexane is added, the vial capped and shaken to produce a standard solution.

10 microliters of standard solution is injected into the HPLC to obtain a chromatogram. Identically, 10 microliters of sample solution is injected into the HPLC to obtain a chromatogram. The chromatograms are compared.

For calculating response factors and ingredient content, the peaks are grouped as:
Internal Standard (I.S.)=Acetophenone
Working Standard=Karathane™
Test Sample=sample being evaluated for isomeric content
Group 1: Sum of the area for 2,4-dinitro-6-octylphenol
Group 2: Sum of the area for 2,4-dinitro-6-octylphenyl crotonates
Group 3: Sum of the area for 2,6-dinitro-4-octylphenyl crotonates $$RF = \frac{\text{Area of } I.S. \text{ peak} \times \text{wt. of Working Standard} \times (\text{percent of Group in Working Standard})}{\text{Area Group} \times \text{weight } I.S. \times 100}$$

An RF factor is calculated for each group.

$$\text{Content (percent)} = \frac{\text{Area of the Group peak} \times \text{weight of } I.S. \times RF \times 100}{\text{Area of the } I.S. \text{ peak} \times \text{weight of Test Sample}}$$

percent Content is calculated for each group using the appropriate RF factor.

For Group 3, the content would be 0 if there were no peaks associated with Group 3. The isomeric percent of Group 2 is then determined by comparing the relative peaks within the group, i.e. 2,4-dinitro-6-(1-methylheptyl)phenyl crotonate 98.5 percent and 2,4-dinitro-6-(1-ethylhexyl)phenyl crotonate 1.2 percent.

The analysis of the product using this normal phase, liquid chromatographic method, is as follows:

| | |
|---|---|
| 2,4-dinitro-6-(1-methylheptyl)phenyl crotonate: | 98.5 percent |
| 2,4-dinitro-6-(1-ethylhexyl)phenyl crotonate: | 1.2 percent |
| 2,4-dinitro-6-(1-methylheptyl)phenol: | 0.3 percent |

Examples 2 and 3

Additional Isomer Analysis of Samples Prepared According to Example I

In a separate analysis, two additional samples prepared according to Example I were analyzed for the active ingredient and impurities using normal phase HPLC with internal standard calibration as outlined below.
Normal Phase High Performance Liquid Chromatography (HPLC)
Preparation of Acetophenone Internal Standard Solution:
Approximately 1 g of Acetophenone was weighed into a 500-mL volumetric flask, the weight was recorded to the nearest 0.1 mg and the flask was filled to volume with hexane.
Preparation of Calibration Solutions:
Calibration Solution #1 was prepared in duplicate by weighing approximately 50 mg of 2,4-dinitro-6-(1-methylheptyl)phenyl crotonate (DNOP) standard, into a vial and 20 mL of the acetophenone internal standard solution was added using a volumetric pipette. A 1 mL aliquot was added to 5 mL of hexane.

Calibration Solution #2 was prepared by weighing approximately 15 mg each of 2,6-dinitro-4-(1-propylpentyl) phenyl crotonate, 2,4-dinitro-6-(1-propylpentyl)phenyl crotonate (propylpentyl isomer), 2,4-dinitro-6-(1-ethylhexyl) phenyl crotonate (Ethylhexyl isomer) and 2,4-dinitro-6-(1-methylheptyl)phenol into a vial and adding 10 mL of hexane. A 1 mL aliquot of the resulting solution was added to a vial containing 20 mL of the acetophenone internal standard solution. A 1 mL aliquot of this solution was added to 5 mL of hexane.

Calibration Solution #3 was prepared by weighing approximately 10 mg of Dinocap, (mixture of 12 isomers, purity 95.3 percent) into a vial and adding 20 mL of the acetophenone internal standard solution using a volumetric pipette. A 1 mL aliquot of the resulting solution was added to 5 mL of hexane.
Calibration Procedure:
The calibration solutions were injected before, during and after the samples, using the following conditions:
Column: Lichrosorb SI-60 5 μm; 250 mm×4.6 mm
Autosampler: Alcott 728
Pump: Varian 9012
Injection: 10 μL
Detector: Applied Biosystems 757
Column Temperature: 30° C.
Column Oven: Phenomenex
Data System: PE/Nelson Access*Chrom
Mobile Phase: 720 mL hexane/280 mL dichloromethane/1 mL polar mix (85 mL dichloromethane/10 mL acetic acid/5 mL ethanol)
Approximate Retention Times:

| | |
|---|---|
| 2,4-dinitro-6-(1-propylpentyl) phenol | 5.79 minutes |
| 2,4-dinitro-6-(1-ethylhexyl) phenol | 5.90 minutes |
| 2,4-dinitro-6-(1-methylhexyl) phenol | 6.13 minutes |
| unknown peak | 6.42 minutes |
| 2,6-dinitro-4-(1-propylpentyl) phenyl crotonate cis | 7.49 minutes |
| 2,6-dinitro-4-(1-ethylhexyl) phenyl crotonate cis | 7.92 minutes |
| 2,6-dinitro-4-(1-methylhexyl) phenyl crotonate cis | 8.15 minutes |
| 2,6-dinitro-4-(1-propylpentyl) phenyl crotonate trans | 9.70 minutes |
| 2,6-dinitro-4-(1-ethylhexyl) phenyl crotonate trans | 10.40 minutes |
| 2,6-dinitro-4-(1-methylhexyl) phenyl crotonate trans | 10.89 minutes |
| 2,4-dinitro-6-(1-propylpentyl) phenyl crotonate cis | 11.30 minutes |
| 2,4-dinitro-6-(1-ethylhexyl) phenyl crotonate cis | 11.53 minutes |
| 2,4-dinitro-6-(1-methylhexyl) phenyl crotonate cis | 12.04 minutes |
| 2,4-dinitro-6-(1-propylpentyl) phenyl crotonate trans | 15.50 minutes |
| 2,4-dinitro-6-(1-ethylhexyl) phenyl crotonate trans | 16.00 minutes |
| 2,4-dinitro-6-(1-methylhexyl) phenyl crotonate trans | 16.98 minutes |
| Acetophenone (ISTD) | 31.82 minutes |

Response factors were calculated for each as described previously. The average of the response factors was used for calibration.
Preparation of Samples for Analysis:
Duplicate weighings of approximately 50 mg (+10 mg), recorded to the nearest 0.1 mg, of EXAMPLES 2 and 3, prepared according to Example 1 were placed into separate vials. To each vial, 20 mL of the acetophenone internal standard solution was added using a volumetric pipette. A 1 mL aliquot of the resulting solution was added to 5 mL of hexane. The samples were analyzed using the same conditions as the standard. Weight percent analysis of EXAMPLES 2 and # are listed in TABLE I.

TABLE I

| Component | EXAMPLE 2 (wt percent) | EXAMPLE 3 (wt percent) |
|---|---|---|
| 2,4-dinitro-6-(1-methylheptyl)phenyl crotonate | 97.9 | 98.0 |
| 2,4-dinitro-6-(1-propylpentyl) phenol | ND | ND |
| 2,4-dinitro-6-(1-ethylhexyl) phenol | ND | ND |
| 2,4-dinitro-6-(1-methylheptyl) phenol | 0.23 | 0.35 |
| unknown at 6.4 min | 0.02 | 0.03 |
| 2,6-dinitro-4-(1-propylpentyl) phenyl crotonate cis | ND | ND |
| 2,6-dinitro-4-(1-ethylhexyl) phenyl crotonate cis | ND | ND |
| 2,6-dinitro-4-(1-methylheptyl) phenyl crotonate cis | ND | ND |
| 2,6-dinitro-4-(1-propylpentyl) phenyl crotonate trans | 0.07 | 0.03 |
| 2,6-dinitro-4-(1-ethylhexyl) phenyl crotonate trans | 0.03 | 0.007 |
| 2,6-dinitro-4-(1-methylheptyl) phenyl crotonate trans | ND | ND |
| 2,4-dinitro-6-(1-propylpentyl) phenyl crotonate cis | ND | ND |
| 2,4-dinitro-6-(1-ethylhexyl) phenyl crotonate cis | ND | ND |
| 2,4-dinitro-6-(1-propylpentyl) phenyl crotonate trans | ND | ND |
| 2,4-dinitro-6-(1-ethylhexyl) phenyl crotonate trans (LC) | 1.4 | 1.3 |
| Other | 1.45 | 1.283 |
| Mass Balance (Wt. percent) | 101.1 | 101.0 |

Not Detected (ND)
Limit of Detection (LOD) = 0.02 percent

Testing on Plants:

The composition of Example 1 was evaluated for fungicidal efficacy in a greenhouse on 9 diseases caused by plant pathogenic fungi (TABLE II). The plant cultivars used in this study were Ugni Blanc (grape), Bovowinka (crab apple), HH88 (sugar beet), M-9 (rice) and Yuma (wheat). Broad leaf plants and rice were grown in a soil-less peat-based potting mixture (Metromix), and wheat was grown in a 50/50 mix of mineral soil and Metromix. The wheat was grown at a temperature of 20° C. and all the other plants were grown at 25° C. Apple seeds were soaked in water, incubated for a short time in 200 ppm solution of benlate and washed again with water. The moist seeds were stored in a closed container at 7° C. (45° F.) and washed once a week with water until the radical had emerged 3 mm (approximately 30 days). The seeds were then planted and seedlings with 4-6 leaves were typically ready for inoculation 3 weeks later.

High Volume Application Studies.

The composition of Example 1 was applied to seedlings at 100, 50, 25, and 12.5 ppm using a high volume spray application. The composition was formulated in water and serial dilutions made and then brought up to volume by adding water solution. Plants were sprayed to run off with 15 mL of solution on a turn-table sprayer with two opposing 4JAUPM air atomization nozzles (Spraying Systems) at a pressure of 138 kPa. Volume of spray solution on a per hectare basis is approximately 4000 L/ha. Plants were inoculated with the pathogens 1 day after application of the composition of Example 1 (1 day protectant test), incubated in a dew chamber for 24 hours with 100 percent relative humidity and then moved to an appropriate environment for disease expression for the duration of the test. Three replicate pots were sprayed for each pathogen/composition combination. Plants were evaluated for percent disease incidence 7-14 days after inoculation and the average percent disease control determined. Results are listed in TABLES III and IV.

Pathogen Propagation and Host Inoculation.

Plants were inoculated with various pathogens 1 day after application of the composition of EXAMPLES 1, 4-5 (protectant tests) and 2 days before application for EXAMPLES 6-7 (curative tests). For all wheat trials, compositions were applied at growth stage 1.2, when the second leaf was expanded to ½ of its final size (12 days after seeds were first watered). Information on the growth stages of other plant species at the time composition application and on the propagation and inoculation procedures associated with each pathogen is given below.

TABLE II

Plant pathogens and host plants used in greenhouse evaluation.

| Host Plant | Disease Name | Causal Organism | Bayer Code |
|---|---|---|---|
| Wheat | Powdery Mildew | *Erysiphe graminis* f.sp *tritici* | ERYSGT |
| Wheat | Brown Rust | *Puccinia recondita* | PUCCRT |
| Apple | Scab | *Venturia inaequalis* | VENTIN |
| Grapes | Powdery mildew | *Uncinula necator* | UNCINE |
| Cucumbers | Powdery mildew | *Erysiphe cichoracearum* | ERYSCI |

ERYSGT: Wheat seedlings were infected with fresh spores from the obligate pathogen ERYSGT by shaking heavily infected wheat plants over them. Plants that had been dusted with ERYSGT spores were incubated in the greenhouse at 22° C. until disease symptoms had fully developed (usually 7 days).

ERYSCI: Cucumber seedlings were infected with fresh spores from the obligate pathogen ERYSCI by spraying a spore suspension on them. Plants were sprayed to run-off. The seedlings were incubated in the greenhouse at 22° C. until disease symptoms had fully developed (usually 10 days).

PUCCRT: Spores of the obligate pathogen PUCCRT were collected from infected plants with a vacuum apparatus and stored at 4° C. Approximately 0.1 g of fresh spores (stored at 4° C. for less than 30 days) was mixed with several drops of Tween 20. The thick spore paste was diluted to 100 ml with water and sprayed to run-off on wheat seed seedlings. Plants inoculated with PUCCRT were kept in a 20° C. dew chamber overnight and then transferred to a 20° C. growth chamber where symptoms developed in 8-9 days.

PYRIOR: Inoculum was produced on PDA grown under white light at 24° C. for 10-12 days. The mycelium was scraped off in water, minced in a blender and expressed through several layers of cheesecloth. Spore concentration was adjusted to 50,000/ml and three large drops of Tween 20 were then added for each 100 ml of volume. Twelve day-old rice plants (second leaf fully expanded) were sprayed to run-off with the aqueous spore suspension, placed in a 24° C. dew chamber for 24 hr and then moved to a 24° C. growth chamber until disease symptoms had fully developed (7 days).

VENTIN: Conidia that were previously harvested (up to 6 months earlier) by washing infected leaves in tap water and then freezing the solution at a concentration of 400,000 spores/ml, were used for inoculations. Apple seedlings were sprayed to run-off with the VENTIN inoculum, incubated 24 hr in a 20° C. dew chamber and then moved to an 18° C. growth chamber until disease symptoms developed (8 days). Disease severity was evaluated only on the two youngest leaves at the time of inoculation because older leaves become highly resistant to infection with this pathogen.

UNCINE: Six week-old grape plants, pruned to maintain two fully expanded leaves, were infected with fresh spores from this obligate pathogen by shaking infected plants over them. Plants that had been dusted with UNCINE spores were incubated in the greenhouse at 22° C. until disease symptoms developed (usually 10 days).

TABLE III

High volume test with three plant pathogenic fungi in a high volume screen.

| Pathogen | Rate (ppm) | Percent disease control |
|---|---|---|
| ERYSCI | 200 | ** |
| PUCCRT | 200 | *** |
| PYRIOR | 200 | *** |

\* is 0-49 percent control of disease
\*\* is 50-79 percent control of disease
\*\*\* is 80-100 percent control of disease

TABLE IV

Percent Disease Control

| Material | Rate ppm | ERYSGT | PUCCRT | UNCINE | VENTIN |
|---|---|---|---|---|---|
| Ex. 1 | 100 | *** | *** | *** | *** |
| Ex. 1 | 50 | *** | ** | *** | ** |
| Ex. 1 | 25 | NT | * | *** | ** |
| Ex. 1 | 12.5 | NT | * | *** | ** |
| Azoxystrobin | 25 | NT | NT | *** | NT |
| Fenarimol | 25 | NT | NT | NT | *** |
| untreated | | * | * | * | * |

\* is 0-49 percent control of disease
\*\* is 50-79 percent control of disease
\*\*\* is 80-100 percent control of disease
NT is not tested Synergy Examples Combinations of Example 1 and named fungicides show synergistic activity on phytopathogenic disease of crop plants. A synergistic effect exists whenever the action of an active ingredient combination is greater than the sum of the action of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967)

X=percent action by active ingredient I using p ppm of active ingredient

Y=percent action by active ingredient II using q ppm of active ingredient

According to Colby the expected additive action of active ingredients I+II using p+q ppm of active ingredients is $$E = X + Y - (X*Y)/100$$

If the action actual observed (O) is greater than the expected action (E), then the action of the combination is super additive, that is, there is a synergistic effect.

Alternatively the synergistic action may also be determined from the dose response curves using the so called WADLEY method. (EPPO—Bulletin 16, 1986, 651-657)

Example 4

Synergistic Combination of Example 1 and Mancozeb

Protectant activity of combinations against wheat brown rust (PUCCRT).

1 day protectant glasshouse studies.

TABLE V

| Mixing partner Rate (ppm) | Ex. 1 (ppm) | Observed Percent CONTROL | Predicted Percent CONTROL | SF Colby |
|---|---|---|---|---|
| Ex. 1 | none | 75.00 | 68.63 | |
| Ex. 1 | none | 50.00 | 33.33 | |
| Ex. 1 | none | 25.00 | 11.76 | |
| Ex. 1 | none | 12.50 | 0.00 | |
| Mancozeb 200.00 | none | 88.24 | | |
| Mancozeb 100.00 | none | 58.82 | | |
| Mancozeb 50.00 | none | 5.88 | | |
| Mancozeb 25.00 | none | 0.00 | | |
| Mancozeb 100.00 | 12.50 | 82.35 | 58.82 | 1.40 |
| Mancozeb 50.00 | 12.50 | 52.94 | 5.88 | 9.00 |
| Mancozeb 25.00 | 12.50 | 25.49 | 0.00 | 25.49 |
| Mancozeb 100.00 | 25.00 | 86.27 | 63.67 | 1.36 |
| Mancozeb 50.00 | 25.00 | 80.39 | 16.96 | 4.74 |
| Mancozeb 25.00 | 25.00 | 33.33 | 11.76 | 2.83 |
| Mancozeb 100.00 | 50.00 | 97.65 | 72.55 | 1.35 |
| Mancozeb 50.00 | 50.00 | 86.67 | 37.25 | 2.33 |
| Mancozeb 25.00 | 50.00 | 76.47 | 33.33 | 2.29 |
| Mancozeb 100.00 | 75.00 | 97.25 | 87.08 | 1.12 |
| Mancozeb 50.00 | 75.00 | 94.12 | 70.47 | 1.34 |
| Mancozeb 25.00 | 75.00 | 76.47 | 68.63 | 1.11 |

Efficacy of the combinations of mancozeb and Example 1 with ratios ranging from 8:1 to 3:1 showed synergistic activity.

Example 5

Synergistic combination of Example 1 and Myclobutanil

Protectant activity of combinations against wheat brown rust (PUCCRT).

1 day protectant glasshouse studies.

TABLE VI

| | Mixing partner rate (ppm) | Ex. 1 (ppm) | Observed Percent CONTROL | Predicted Percent CONTROL | SF Colby |
|---|---|---|---|---|---|
| Ex. 1 | none | 75.00 | 68.63 | | |
| Ex. 1 | none | 50.00 | 33.33 | | |
| Ex. 1 | none | 25.00 | 11.76 | | |
| Ex. 1 | none | 12.50 | 0.00 | | |
| Myclobutanil | 18.75 | none | 84.31 | | |
| Myclobutanil | 12.50 | none | 74.51 | | |
| Myclobutanil | 6.25 | none | 27.45 | | |
| Myclobutanil | 3.13 | none | 0.00 | | |
| Myclobutanil | 12.50 | 12.50 | 72.55 | 74.51 | 0.97 |
| Myclobutanil | 6.25 | 12.50 | 56.86 | 27.45 | 2.07 |
| Myclobutanil | 3.13 | 12.50 | 11.76 | 0.00 | 11.76 |
| Myclobutanil | 12.50 | 25.00 | 84.31 | 77.51 | 1.09 |
| Myclobutanil | 6.25 | 25.00 | 70.59 | 35.99 | 1.96 |
| Myclobutanil | 3.13 | 25.00 | 45.10 | 11.76 | 3.83 |
| Myclobutanil | 12.50 | 50.00 | 98.04 | 83.01 | 1.18 |
| Myclobutanil | 6.25 | 50.00 | 96.47 | 51.63 | 1.87 |
| Myclobutanil | 3.13 | 50.00 | 92.94 | 33.33 | 2.79 |
| Myclobutanil | 6.25 | 75.00 | 92.94 | 77.24 | 1.20 |
| Myclobutanil | 3.13 | 75.00 | 84.31 | 68.63 | 1.23 |

Synergistic activity for Sterol biosynthesis inhibition; C14-demethylase inhibition (SBI class I), illustrative example myclobutanil. Efficacy of the combinations of myclobutanil and Example 1 with ratios ranging from 1:24 to 1:4 showed synergistic activity.

Example 6

Synergistic Combination of Example 1 and Spiroxamine

Curative activity of combinations against wheat powdery mildew (ERYSGT). 2 day curative glasshouse studies.

TABLE VII

| | Mixing partner rate (ppm) | Ex. 1 (ppm) | Observed Percent CONTROL | Predicted Percent CONTROL | SF Colby |
|---|---|---|---|---|---|
| Ex. 1 | none | 75.00 | 23.00 | | |
| Spiroxamine | 12.50 | none | 15.00 | | |
| Spiroxamine | 12.50 | 75.00 | 65.00 | 34.75 | 1.88 |

Confirmation of synergistic activity for Sterol biosynthesis inhibition; D14 reductase and D8 isomerase in sterol biosynthesis (SBI class II), illustrative example spiroxamine. Efficacy of the combinations of spiroxamine and Example 1 with a 1:4 ratio showed synergistic activity.

Example 7

Synergistic combination of Example 1 and Azoxystrobin

Curative activity of combinations against wheat powdery mildew (ERYSGT).

2 day curative glasshouse studies.

TABLE VIII

| | Mixing partner rate (ppm) | Ex. 1 (ppm) | Observed Percent CONTROL | Predicted Percent CONTROL | SF Colby |
|---|---|---|---|---|---|
| Ex. 1 | none | 75.00 | 23.00 | | |
| Azoxystrobin | 6.25 | none | 13.00 | | |
| Azoxystrobin | 12.50 | none | 15.00 | | |
| Azoxystrobin | 25 | none | 15 | | |
| Azoxystrobin | 75 | none | 52 | | |
| Azoxystrobin | 100 | none | 79 | | |
| Azoxystrobin | 6.25 | 75 | 42 | 33.41 | 1.27 |
| Azoxystrobin | 12.50 | 75 | 54 | 34.91 | 1.54 |
| Azoxystrobin | 25 | 75 | 73 | 34.91 | 2.09 |
| Azoxystrobin | 75 | 75 | 97 | 63.02 | 1.54 |
| Azoxystrobin | 100 | 75 | 98 | 83.77 | 1.17 |

Synergistic activity for fungicides acting as respiration inhibitors at complex III; cytochrome bc1 at Qo site. (QoI fungicides); illustrative example azoxystrobin. Efficacy of the combinations of azoxystrobin and Example 1 with ratios ranging from 1:12 to 4:3 showed synergistic activity.

What is claimed is:

1. An isomeric composition comprising: from 0.1 to 99.9 weight percent 2,4-dinitro-6-(1-methylheptyl)phenyl ester,
   from 0.1 to 99.9 weight percent 2,4-dinitro-6-(1-ethylhexyl)phenyl ester,
   from 0.1 to 99.9 weight percent 2,4-dinitro-6-(1-propylpentyl)phenyl ester,
   from 0.1 to 99.9 weight percent 2,6-dinitro-4-(1-methylheptyl)phenyl ester,
   from 0.1 to 99.9 weight percent 2,6-dinitro-4-(1-ethylhexyl)phenyl ester, and
less than 0.1 weight percent 2,6-dinitro-4-(1-propylpentyl) phenyl esterbased on the total weight of the isomeric composition, wherein said isomeric composition has fungicidal activity against *Unicinula necator*.

2. The isomeric composition of claim 1 comprising:
   at least 95 weight percent of 2,4-dinitro-6-(1-methylheptyl)phenyl ester,
   less than 3 weight percent of 2,4-dinitro-6-(1-ethylhexyl) phenyl ester, and
   less than 0.1 weight percent of 2,6-dinitro-4-(1-propylpentyl)phenyl ester,
based on the total weight of the isomeric composition.

3. The isomeric composition of claim 1 wherein each ester of the isomeric composition is a crotonate.

4. A fungicidal composition, useful for protecting a plant against attack by a phytopathogenic organism and/or treatment of a plant infested by a phytopathogenic organism, comprising
   I) the isomeric composition of claim 1, and
   II) a phytologically acceptable carrier material.

5. The fungicidal composition of claim 4 wherein, the isomeric composition is
   at least 95 weight percent of 2,4-dinitro-6-(1-methylheptyl)phenyl ester,
   less than 3 weight percent of 2,4-dinitro-6-(1-ethylhexyl) phenyl ester, and less than 0.1 weight percent of 2,6-dinitro-4-(1-propylpentyl)phenyl ester, based on the total weight of the isomeric composition.

6. The fungicidal composition of claim 4 wherein each ester of the isomeric composition is a crotonate.

7. A synergistic fungicidal composition comprising the isomeric composition of claim 1 and at least one agriculturally active compound selected from the group consisting of: mancozeb, myclobutanil, and spiroxamine.

8. A synergistic fungicidal composition comprising the isomeric composition of claim 2 and at least one agriculturally active compound selected from the group consisting of: mancozeb, myclobutanil, and spiroxamine.

9. A synergistic fungicidal composition comprising the isomeric composition of claim 3 and at least agriculturally active compound selected from the group consisting of: mancozeb, myclobutanil, and spiroxamine.

10. A method for the control of fungal attack comprising applying to the plant, foliage, locus of the fungus, or to a locus in which the infestation is to be prevented, a fungicidal effective amount of the isomeric composition of claim 1 or the composition of claim 7.

11. The method according to claim 10, wherein the isomeric composition comprises:
    at least 95 weight percent of 2,4-dinitro-6-(1-methylheptyl)phenyl ester,
    less than 3 weight percent of 2,4-dinitro-6-(1-ethylhexyl) phenyl ester, and
    less than 0.1 weight percent of 2,6-dinitro-4-(1-propylpentyl)phenyl ester, based on the total weight of the isomeric composition.

12. The method according to claim 10 wherein each ester of the isomeric composition is a crotonate.

* * * * *